United States Patent [19]

McAfee et al.

[11] 4,450,283

[45] May 22, 1984

[54] PLATINUM-STYRENE COMPLEXES WHICH PROMOTE HYDROSILATION REACTIONS

[75] Inventors: Richard C. McAfee, Tecumseh; James Adkins, Adrian; Richard L. Miskowski, Jackson, all of Mich.

[73] Assignee: SWS Silicones Corporation, Adrian, Mich.

[21] Appl. No.: 468,118

[22] Filed: Feb. 18, 1983

Related U.S. Application Data

[62] Division of Ser. No. 230,462, Feb. 2, 1981, Pat. No. 4,394,317.

[51] Int. Cl.$^3$ .................. C07F 7/08; C07F 7/10; C07F 7/18
[52] U.S. Cl. ...................................................... 556/479
[58] Field of Search ........................................ 556/479

[56] References Cited

U.S. PATENT DOCUMENTS 4,398,010 8/1983 Adkins .......................... 556/479 X Primary Examiner—Paul F. Shaver

[57] ABSTRACT

Platinum-styrene complexes are prepared by reacting a platinum halide with styrene or substituted styrenes in the presence of a basic material for a sufficient amount of time to form a complex having more than one and less than four gram atoms of halogen per gram atom of platinum.

These platinum-styrene complexes may be used to promote the addition of organosilicon compounds having at least one $\equiv$SiH group per molecule to a compound containing aliphatic unsaturation.

10 Claims, No Drawings

1

PLATINUM-STYRENE COMPLEXES WHICH PROMOTE HYDROSILATION REACTIONS

This is a division of application Ser. No. 230,462, filed Feb. 2, 1981, now U.S. Pat. No. 4,394,317.

The present invention relates to platinum complexes and more particularly to platinum-styrene complexes having improved stability which promote hydrosilation reactions.

BACKGROUND OF THE INVENTION

Various platinum compounds and complexes have been used heretofore to promote hydrosilation reactions. The platinum compounds and complexes which have been used to promote hydrosilation reactions such as the addition of organosilicon compounds containing ≡SiH groups to compounds containing aliphatic unsaturation are compounds such as chloroplatinic acid, platinum chloride-olefin complexes, platinum chloride-cyclopropane and complexes derived from the reaction of alcohols, ethers, aldehydes, ketones and vinyl siloxanes with chloroplatinic acid.

While chloroplatinic acid and elemental platinum may be used as catalysts for hydrosilation reactions, they have certain disadvantages. For example, chloroplatinic acid is insoluble in many organic solvents and is not always effective at low concentrations. Moreover, these catalysts are subject to poisoning in the presence of a number of common materials. The disadvantages of elemental platinum and chloroplatinic acid with respect to poisoning and speed of reaction have been overcome by the use of the platinum compounds described above, such as the platinum-olefin complexes described in U.S. Pat. Nos. 3,159,601 and 3,159,662 to Ashby. Faster and more active catalysts are described in U.S. Pat. Nos. 3,715,334; 3,775,452; and 3,814,730 to Karstedt, in which platinum vinyl siloxane complexes are treated with a base material to form a catalyst in which the halogen to platinum ratio is about 1:1 or less than 1:1.

It has been found that a platinum-styrene complex which is formed in the presence of a basic material and has a halogen to platinum ratio of more than one, but less than four gram atoms of halogen per gram atom of platinum, is substantially more stable than other platinum complexes and maintains its level of activity for longer periods of time.

Therefore, it is an object of this invention to provide a novel platinum catalyst. Another object of this invention is to provide a platinum catalysts for effecting the addition of SiH-containing organosilicon compounds to unsaturated organic compounds. Still another object of this invention is to provide a catalyst which is highly reactive at room temperature and is more effective at lower concentrations. A further object of this invention is to provide a catalyst which is more stable and maintains its level of activity for longer periods of time.

SUMMARY OF THE INVENTION

The foregoing objects and others which will become apparent from the following description are accomplished in accordance with this invention, generally speaking, by providing a process for preparing a platinum complex which comprises reacting a platinum halide with styrene or substituted styrenes in the presence of a basic material to form a platinum complex which contains more than one and less than four gram atoms of halogen per gram atom of platinum. The resultant complex may be used to promote the addition of organosilicon compounds containing silicon-bonded hydrogen to unsaturated organic compounds.

DETAILED DESCRIPTION OF THE INVENTION

Platinum complexes are known in the art and their preparation and properties are described, for example, in "Coordination Compounds of Olefins with Metallic Salts," R. N. Keller, Chemical Reviews, 1940-41, 27-28, pages 229-267; and Joy and Orchin, Journal of the American Chemical Society, 81, pages 305-311 (1959). The olefin portion of the platinum complexes of this invention is styrene and ring substituted styrenes. Examples of substituted styrenes are alkyl ring substituted styrenes such as m-methylstyrene, p-ethylstyrene, p-ethoxystyrene and the like. The platinum complexes of this invention are prepared by reacting a platinum halide with styrene or substituted styrenes in the presence of a basic material. Examples of suitable basic materials are alkali metal carbonates, such as sodium carbonate, potassium carbonate and sodium bicarbonate.

Although, the amount of base employed is not critical, a sufficient amount of base should be present to neutralize at least some of the available halogen. Even though less than a stoichiometric amount can be employed, it is preferred that a stoichiometric amount or even a slight excess be employed in order to neutralize enough of the available halogen to form a complex containing more than one and less than four gram atoms of halogen per gram atom of platinum.

The platinum-styrene complex of this invention is prepared by reacting a platinum halide, such as chloroplatinic acid, with styrene in the presence of a base and preferably an alcohol at a temperature of from 0° to 130° C., preferably at a temperature from 25° to 100° C. and more preferably at a temperature of from 40° to 60° C. Also, it is possible to form a platinum-styrene complex in the absence of the base and thereafter react the platinum complex with the basic material to substantially reduce the halogen content of the resultant catalyst.

The reaction between the platinum halide, styrene and base is dependent on the amount of base present and the temperature. Thus, the reaction time varies inversely with the temperature, i.e., the higher the temperature, the shorter the reaction time and conversely, the lower the temperature, the longer the reaction time. When the reaction temperature is in the preferred range, i.e., from 40° to 60° C., the reaction time varies from about one hour to about 0.25 hours.

The reaction may be conducted at atmospheric pressure or below or above atmospheric pressure. Preferably, the reaction is conducted at atmospheric pressure.

The platinum halide such as chloroplatinic acid which is employed in the reaction with the olefin is commercially available in the form of chloroplatinic acid hexahydrate, $H_2PtCl_6.6H_2O$, however, the material can be used in the anhydrous form or it can be used as the hexahydrate.

Suitable solvents which may be employed in the preparation of the platinum-styrene complexes of this invention are alcohols having from 1 to 6 carbon atoms such as methanol, ethanol, propanol, butanol and hexanol and aromatic hydrocarbon solvents such as benzene, toluene and xylene. It is preferred that the solvent be an alcohol and more preferably ethanol. Mixtures of alcohols or alcohols and aromatic hydrocarbons may be used. The amount of solvent is not critical and may range from about 1 to 100 parts and more preferably from about 10 to 50 parts per part of platinum halide.

The platinum-styrene complexes of this invention are effective for the addition of organosilicon compounds containing silicon-bonded hydrogen to organic compounds having carbon-carbon unsaturation. The catalysts of this invention are effective for the addition reactions described in U.S. Pat. Nos. 2,823,218 to Speir et al, 2,970,150 to Bailey and 3,220,970 to Lamoreaux.

Suitable monomeric silicon compounds and organosilicon compounds containing silicon-bonded hydrogen which may be used in the present invention are those represented by the formula

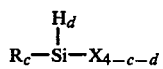

in which R is an alkyl, cycloalkyl, alkaryl, aralkyl, haloalkyl or haloaryl radicals, X is a hydrolyzable radical, such as halogen, alkoxy radicals, aryloxy radicals and acyloxy (OOCR) radicals; c is a number of from 0 to 3, d is a number of from 1 to 3; and the sum of c and d is from 1 to 4. When more than one R radical is present in the compound the various R radicals may be the same or different.

Among the radicals represented by R are alkyl radicals, e.g., methyl, ethyl, propyl, octyl and octadecyl radicals; cycloalkyl radicals such as the cyclohexyl and cycloheptyl radicals; aryl radicals such as the phenyl, biphenyl, alkaryl radicals such as tolyl and xylyl radicals; aralkyl radicals such as the benzyl and phenylethyl radicals; haloaryl radicals and haloalkyl radicals such as the chlorophenyl, chloromethyl and the dibromophenyl radicals. Preferably, R is a methyl or a mixture of methyl and phenyl radicals.

Examples of suitable silicon compounds represented by the above formula which can be employed in the present invention are: methyldichlorosilane, phenyldichlorosilane, diethylchlorosilane, dimethylethoxysilane, diphenylchlorosilane, dichlorosilane, dibromosilane, pentachlorodisiloxane, and the like.

Suitable silicon-bonded hydrogen containing which may may be used in the present invention are those in which each molecule contains at least one silicon-bonded hydrogen. Suitable examples of such compounds are organopolysiloxanes and various polysilalkylene compounds containing, for example, an —Si—Y—Si— linkage in which Y is a divalent hydrocarbon radical having from 1 to 8 carbon atoms or a nitrogen atom, such as organosilazanes, having the —Si—N—SI— linkage in the polymer.

Suitable examples of organopolysiloxanes are polymers and copolymers containing up to one or more of the units having the formulae: $R_3SiO_{0.5}$, $R_2SiO$, $RSiO_{1.5}$ or $SiO_2$ along with at least one unit per molecule having the formulae: $RHSiO$, $R_2HSiO_{0.5}$, $HSiO_{1.5}$, $H_2SiO$, $RH_2SiO_{0.5}$ wherein R is the same as above. Any of the silicon hydrogen compounds described above, are operative in the practice of the present invention, however, it is preferred that the silicon hydrogen compound be an organopolysiloxane such as an organopolysiloxane $(RHSiO)_n$ or an organopolysiloxane polymer or copolymer having the formula $R_ySiH_zO_{4-y-z}$ where R is the same as above, n is a number of from 1 to 20,000, y is a number of from about 0.5 to 2.49 and z is a number of from 0.001 to 1 and the sum of y and z is a number equal to from 1 to 2.5.

Compounds containing carbon-to-carbon unsaturation, particularly unsaturated compounds containing olefinic or acetylenic unsaturation which can react with the organic compounds described above containing the silicon-bonded hydrogen are monomeric and polymeric compounds containing aliphatic unsaturation. These compounds can contain only carbon and hydrogen or they may also contain another element or elements. Where the aliphatically unsaturated compounds contain an element other than carbon and hydrogen, it is preferred that the other element be oxygen, halogen, nitrogen, silicon or mixtures thereof. Aliphatically unsaturated compounds which may be employed that have a single pair of carbon atoms linked by multiple bonds are for example, ethylene, propylene, butylene, octylene, styrene, butadiene, pentadiene, 2-pentene, 2-divinylbenzene, vinyl acetylene and the like. Preferably the unsaturated compound does not contain more than about 24 carbon atoms in the chain.

Included in the oxygen containing unsaturated compounds which may be employed in the practice of the invention are methylvinylether, divinylether and the like; the monoalkylethers of ethylene glycol, allyl aldehyde, methylvinyl ketone, phenylvinyl ketone, acrylic acid, methylmethacrylate, phenylmethacrylate, vinylacetic acid, vinyl octoate, vinyl acetate, maleic acid, linoleic acid and the like. Other unsaturated compounds which may be employed are cyclic and heterocyclic materials containing aliphatic unsaturation in the ring, such as, cyclohexene, cycloheptene, cyclopentadiene, dihydrofuran, dihydropyrene and the like. The sulfur analogues of the unsaturated oxygen containing materials may also be employed in the practice of this invention. In addition to compounds containing carbon, hydrogen, oxygen and sulfur, compounds containing other elements may also be employed. Thus, halogenated derivatives of any of the materials described above can be employed including the acyl chlorides as well as compounds containing a halogen substituent on a carbon atom. Thus, halogen containing materials include, for example, vinyl chloride, the vinyl chlorophenyl esters, the allyl esters of trichloroacetic acid and the like.

Other types of unsaturated materials which are useful in the practice of this invention include compounds containing nitrogen substituents such as acrylonitrile, allylcyanide, nitroethylene and the like. Unsaturated polymeric materials containing aliphatic unsaturation such as polyester resins prepared from polybasic saturated or unsaturated acids and polyhydric unsaturated alcohols may also be used in the practice of this invention.

Other unsaturated compounds which may be used in the practice of this invention are those compounds containing silicon such as the material commonly referred to as organo-silicon monomers or polymers. The scope of the organosilicon compounds which are applicable to the process is identical to the scope of the silicon-bonded hydrogen compounds useful in the practice of this invention. For example, the unsaturated organosilicon compounds are identical to the silicon-bonded hydrogen compounds, except that the silicon-bonded hydrogen is replaced by silicon-bonded organic radicals containing at least one pair of aliphatic carbon atoms having aliphatic unsaturation. Although it is preferred that the organosilicon compounds be free of silicon-bonded hydrogen atoms, organosilicon compounds containing both silicon-bonded hydrogen atoms and silicon-bonded unsaturated radicals may be used. The only requirement of these unsaturated silicon compounds is that there be at least one unsaturated organic radical attached to a silicon atom per molecule. Thus, the unsaturated organosilicon compounds include silanes, siloxanes, silazanes, as well as monomeric or polymeric materials having silicon atoms joined together by methylene or polymethylene groups or by phenylene groups.

Examples of suitable unsaturated silicon compounds which may be used are methylvinyldichlorosilane, vinyltrichlorosilane, allyltrichlorosilane, methylphenylvinylchlorosilane, phenylvinyldichlorosilane, diallyldichlorosilane, vinylcyanoethyldichlorosilane, cyclic polysiloxanes such as the cyclic trimer of methylvinylsiloxane, cyclic tetramer of methylvinylsiloxane, cyclic pentamer or methylvinylsiloxane, cyclic tetramer of vinylphenylsiloxane, linear or branched vinyl terminated diemthylpolysiloxanes, trimethylsiloxy terminated vinylmethylpolysiloxanes, ethylphenylpolysiloxanes and copolymers thereof.

The ratio of the silicon-bonded hydrogen compound and the unsaturated compound employed can vary over a wide range. Generally, one silicon-bonded hydrogen is equivalent to one olefinic double bond or one-half acetylenic triple bond so that this equivalency establishes the general order of magnitude of the two reactants employed. However, for many purposes it may be desirable to employ an excess of one of the reactants to facilitate the completion of the reaction or to insure that the reaction contains one or more pairs of carbon atoms linked by multiple bonds. In general, however, the ratio of the reactants is selected so that there are present from about 0.5 to 20 silicon-bonded hydrogen linkages available for each unsaturated carbon-carbon double bond and from about 1.0 to 15 silicon-bonded hydrogen linkages for each carbon-carbon triple bond.

To effect the addition reactions of the organosilicon compositions in the presence of the platinum-styrene complexes of this invention, the reactants and catalyst are thoroughly mixed an allowed to react at temperatures of from 10° to 200° C. The time required for the addition reaction is a function of temperature. At a temperature of from about 15° to 175° C. and more preferably from 20° to 150° C., the reaction times can vary from a few seconds up to about 10 minutes or more depending upon the amount of catalyst complex employed.

In some cases, it is desirable to employ a solvent for one or both reactants. The amount of solvent employed is not critical and can vary over a wide range. Obviously, the same material may in some cases serve both as the reactant and as the solvent.

The amount of catalyst employed can vary over a wide range. It is preferred that enough catalyst be employed to provide from about 0.5 to 500 ppm by weight and more preferably from 2 to 500 ppm by weight calculated as platinum and based on the weight of the total composition, including silicon compounds, platinum catalyst and any additional materials.

One of the advantages of the novel catalysts of this invention is that a very small amount of the catalyst will effect the desired reaction between the silicon-bonded hydrogen compound and the unsaturated organic compound. In addition, it has been found that the catalyst retains its level of activity even after storing for prolonged periods of time at elevated temperatures. Furthermore, the activity of the catalyst is such that silicon-bonded hydrogen containing organopolysiloxanes and vinyl containing organopolysiloxanes can be cured very rapidly and therefore used as potting or encapsulating compositions for electrical components on assembly lines.

These organopolysiloxane compositions may contain in addition to the silicon-bonded hydrogen containing organopolysiloxanes, and vinyl containing organopolysiloxanes, other additives such as fillers, i.e., silica, hydrogels, aerogels; treated fillers such as silicas which have been treated with, for example trimethylchlorosilane or hexamethyldisilozane to impart hydrophobic properties thereto, quartz, alumina, glass fibers, diatomaceous earth, organosilicon plasticizers, Ultraviolet stabilizers, heat stabilizers and the like. Other additives which may be included in the compositions are those which retard or inhibit the addition of Si-bonded hydrogen to an aliphatic multiple bond at room temperature. Examples of such additives are benzotriazole, 1,3-divinyl-1, 1,,3,3-tetramethyldisiloxane and/or 2-methyl-3-butyn-2-ol.

The catalysts of this invention are combined with $\equiv$SiH containing compounds and organic compounds containing olefinic unsaturation to form elastomeric compositions. These compositions may be used as potting compounds, sealants, coatings and particularly as dental impression materials.

When the compositions of this invention are to be stored for a period of time prior to use, it is preferred that the catalyst be mixed with a portion of the organosilicon compound containing olefinic unsaturation and stored in one package. The remainder of the organosilicon compound containing olefinic unsaturation is preferably mixed with the organosilicon compound containing silicon-bonded hydrogen and stored as a second package. The two packages can then be mixed together at the appropriate time of their use and molded. If other materials are to be added to the composition, they should be incorporated in the individual packages during their preparation rather than adding those materials during the final mixing of the whole composition.

In preparing dental impression compositions, it is preferred that the organosilicon compound containing olefinic unsaturation be a diorganopolysiloxane containing terminal triorganosiloxy groups in which at least one vinyl group is present in each of the triorganosiloxy groups be mixed at room temperature with an organopolysiloxane containing at least three silicon-bonded hydrogen atoms per molecule and the platinum-styrene complex of this invention. Other materials which may be added are additives such as the fillers described above, pigments, flavoring substances and plasticizers. The dental impression compositions of this invention can be used in accordance with the conventional methods of working when using dental impression compositions and employing the devices customarily used for such purposes.

Various embodiments of the invention are illustrated in the following examples in which all parts are by weight unless otherwise specified.

PREPARATION OF PLATINUM-STYRENE COMPLEX

Example 1

A platinum-styrene complex is prepared by adding 6 parts of sodium bicarbonate to a mixture containing 3 parts of chloroplatinic acid ($H_2PtCl_6 \cdot 6H_2O$), 6 parts of styrene and 50 parts of ethanol. The mixture is heated to reflux temperature, (about 55° C.) and refluxed for about 35 minutes with agitation, and then cooled to room temperature. The resultant mixture which contains orange crystals is filtered and the crystals washed with about 30 parts of acetone. About 30 parts of xylene are added to the filtrate which results in the formation of crystals. This mixture is filtered and the orange crystals are recovered and dried. Analysis of these crystals indicates that a platinum-styrene complex is formed having a platinum to chloride ratio of 1:3.1.

EXAMPLE 2

The procedure of Example 1 is repeated except that the mixture is heated at 60° C. for 38 minutes. The resultant product has a platinum to chloride ratio of 1:1.9.

Comparison Example 3

The procedure of Example 1 is repeated except that the mixture is heated at 70° C. for 55 minutes. The resultant product has a platinum to chloride ratio of 1:0.9.

Comparison Example 4

The procedure of Example 1 is repeated except that 6 parts of 1-dodecene are substituted for the styrene.

A catalyst is obtained having a platinum to chloride ratio of 1:2.8.

Comparison Example 5

The procedure of Example 1 is repeated except that the sodium bicarbonate is omitted. The resultant catalyst contains a platinum to chloride ratio of 1:4.0.

PREPARATION OF CROSSLINKED COMPOSITION

Example 6

(a) A mixture is prepared by adding 3 parts of fumed silica and 100 parts of quartz powder to 7 parts of a methylhydrogenpolysiloxane having a viscosity of 50 cs. at 25° C. and 100 parts of vinyl terminated dimethylpolysiloxane having a viscosity of 500 cs. at 25° C.

(b) The platinum-styrene complexes prepared in the above examples are each dissolved in isopropanol to form a solution containing 0.75 percent by weight of elemental platinum. About 1.6 parts of the platinum-styrene complex solutions are added to 100 parts of vinyl terminated dimethylpolysiloxane having a viscosity of 500 cs. at 25° C. The isopropanol is removed at reduced pressure and then 100 parts of quartz powder and 3 parts of fumed silica are added to the vinyl terminated dimethylpolysiloxane catalyzed mixture. The resultant mixture containing about 60 ppm of platinum, calculated as elemental platinum, is stored for three days at room temperature.

A portion of each mixture is heated at 60° C. for various periods of time, cooled to room temperature and then combined with composition (a) above in equal parts and the time required for crosslinking "working time" is observed. A portion of each mixture is also stored at room temperature and combined with equal parts of (a) above. The stability of the catalyst is illustrated in the following table by changes in the "working times".

TABLE

| | | Heat Aging Stability Data | | |
|---|---|---|---|---|
| | | Heat Aging | | |
| Example No. | Ratio Pt:Cl | Time (Hrs.) | Temperature (°C.) | Working Time (Seconds) |
| 1 | 1:3.1 | 24 | 60° | 50 |
| | | 72 | 25° | 50 |
| | | 72 | 60° | 50 |
| | | 120 | 25° | 50 |
| | | 120 | 60 | 35 |
| | | 240 | 25° | 40 |
| | | 240 | 60° | 40 |
| 2 | 1:1.9 | 24 | 60° | 47 |
| | | 72 | 25° | 49 |
| | | 72 | 60° | 50 |
| | | 120 | 25° | 53 |
| | | 120 | 60° | 45 |
| | | 240 | 25° | 48 |
| | | 240 | 60° | 45 |
| 3 | 1:0.9 | 24 | 60° | >600 |
| | | 72 | 25° | >600 |
| | | 72 | 60° | >600 |
| 4 | 1:2.8 | 24 | 60° | >600 |
| | | 72 | 25° | 50 |
| | | 72 | 60° | >600 |
| 5 | 1:4.0 | 8 | 60° | >600 |
| | | 24 | 60° | >600 |

The heat aging tests in the above table show that a catalyst composition having a platinum to chloride ratio of less than 1 and 4 or more gram atoms of chloride per gram atom of platinum does not maintain its level of activity over a long period of time.

What is claimed is:

1. A process for the addition of an organosilicon compound containing silicon-bonded hydrogen to an organic compound having carbon-carbon unsaturation which comprises mixing an organosilicon compound having silicon-bonded hydrogen with an organic compound having carbon-carbon unsaturation in the presence of a platinum-olefinic hydrocarbon complex containing more than one but less than 4 gram atoms of halogen per gram atom of platinum, said platinum-olefinic hydrocarbon complex is obtained from the reaction of a platinum halide and an olefinic hydrocarbon selected from the group consisting of styrene and ring substituted styrenes in the presence of a basic material.

2. The process of claim 1, wherein the organosilicon compound containing silicon-bonded hydrogen is represented by the formula

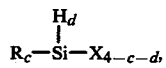

where R is selected from the group consisting of alkyl, cycloalkyl, aryl, alkaryl, aralkyl, haloalkyl and haloaryl radicals, X is a hydrolyzable radical, c is a number of from 0 to 3, d is a number of from 1 to 3 and the sum of c and d is from 1 to 4.

3. The process of claim 1, wherein the organosilicon compound containing silicon-bonded hydrogen is an organopolysiloxane represented by the formula

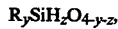

where R is selected from the group consisting of alkyl, cycloalkyl, aryl, alkaryl, aralkyl, haloalkyl and haloaryl radicals, X is a hydrolyzable radical, y is a number of from 0.5 to 2.49, z is a number of from 0.001 to 1 and the sum of y and z is a number of from 1 to 2.5.

4. The process of claim 1, wherein from 0.5 to 20 silicon-bonded hydrogen groups are present for each unsaturated carbon-carbon double bond.

5. The process of claim 1, wherein the mixture containing the organosilicon compound having silicon-bonded hydrogen and the organic compound having carbon-carbon unsaturation and platinum-olefinic hydrocarbon complex is reacted at a temperature of from 10° to 200° C.

6. The process of claim 1, wherein the platinum-olefinic hydrocarbon complex is present in an amount of from 0.5 to 500 ppm by weight of elemental platinum based on the weight of the mixture.

7. The process of claim 1, wherein the platinum-olefinic hydrocarbon complex is prepared in the presence of an alcohol having from 1 to 6 carbon atoms.

8. The process of claim 1, wherein the platinum-olefinic hydrocarbon complex is reacted at a temperature up to 150° C. in the presence of a basic material.

9. The process of claim 1, wherein the basic material is selected from the group consisting of alkali metal carbonates and alkali metal bicarbonates.

10. The process of claim 1, wherein the platinum-olefinic hydrocarbon complex is a platinum-styrene complex.

* * * * *